United States Patent
Cho et al.

(10) Patent No.: US 9,583,787 B2
(45) Date of Patent: Feb. 28, 2017

(54) ADDITIVE FOR ELECTROLYTE AND ELECTROLYTE AND LITHIUM SECONDARY BATTERY

(71) Applicant: Samsung SDI Co., Ltd., Yongin-si, Gyeonggi-do (KR)

(72) Inventors: In-Haeng Cho, Yongin-si (KR); Woo-Cheol Shin, Yongin-si (KR); Sang-Il Han, Yongin-si (KR); Sang-Hoon Kim, Yongin-si (KR); Byung-Joo Chung, Yongin-si (KR); Duck-Hyun Kim, Yongin-si (KR); Myung-Hwan Jeong, Yongin-si (KR); Jung-Yi Yu, Yongin-si (KR); Jung-Hyun Nam, Yongin-si (KR); Seung-Tae Lee, Yongin-si (KR); Tae-Hyun Bae, Yongin-si (KR); Mi-Hyun Lee, Yongin-si (KR); Eon-Mi Lee, Yongin-si (KR); Ha-Rim Lee, Yongin-si (KR); Moon-Sung Kim, Yongin-si (KR); E-Rang Cho, Yongin-si (KR); Dong-Myung Choi, Yongin-si (KR); Pavel Alexandrovich Shatunov, Yongin-si (KR); Alexey Tereshchenko, Yongin-si (KR); Denis Chernyshov, Yongin-si (KR); Makhmut Khasanov, Yongin-si (KR); Vladimir Egorov, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 354 days.

(21) Appl. No.: 14/281,731

(22) Filed: May 19, 2014

(65) Prior Publication Data

US 2015/0010810 A1    Jan. 8, 2015

Related U.S. Application Data

(60) Provisional application No. 61/842,250, filed on Jul. 2, 2013.

(51) Int. Cl.
*H01M 10/40* (2006.01)
*H01M 10/36* (2010.01)
(Continued)

(52) U.S. Cl.
CPC ......... *H01M 10/0567* (2013.01); *C07F 5/022* (2013.01); *H01M 10/052* (2013.01);
(Continued)

(58) Field of Classification Search
CPC ......... H01M 10/0567; H01M 10/0525; H01M 10/052; H01M 10/36; C07F 5/022
See application file for complete search history.

(56) References Cited

U.S. PATENT DOCUMENTS

| 6,924,066 B2 | 8/2005 | Heider et al. |
| 8,168,806 B2 | 5/2012 | Wietelmann et al. |
| 2008/0193854 A1 | 8/2008 | Yamaguchi et al. |

FOREIGN PATENT DOCUMENTS

| JP | 2009-266644 | 11/2009 |
| KR | 10-2000-0068159 A | 11/2000 |

OTHER PUBLICATIONS

EPO Search Report dated Oct. 28, 2014, for corresponding European Patent application 14162380.1, (11 pages).
(Continued)

*Primary Examiner* — Kenneth Douyette
(74) *Attorney, Agent, or Firm* — Lewis Roca Rothgerber Christie LLP

(57) ABSTRACT

An additive, the additive being for an electrolyte for a lithium secondary battery and represented by Chemical Formula 1:

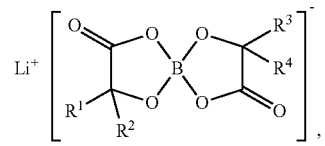

$R^1$ to $R^4$ each independently being hydrogen or a non-polar hydrocarbon group, is disclosed. An electrolyte, the electrolyte being for a lithium secondary battery and including: a non-aqueous organic solvent; a lithium salt; and the additive is also disclosed. A lithium secondary battery including: a positive electrode; a negative electrode facing the positive
(Continued)

electrode; and a separator between the positive electrode and the negative electrode, the separator being impregnated with an electrolyte including the additive, is also disclosed.

19 Claims, 9 Drawing Sheets

(51) Int. Cl.
  C07F 5/02 (2006.01)
  H01M 10/0567 (2010.01)
  H01M 10/052 (2010.01)
  H01M 10/0525 (2010.01)
  H01M 10/39 (2006.01)

(52) U.S. Cl.
  CPC ........ *H01M 10/0525* (2013.01); *H01M 10/36* (2013.01); *H01M 10/39* (2013.01); *Y02E 60/122* (2013.01)

(56) References Cited

OTHER PUBLICATIONS

Allen, J.L., et al., *Lithium bis (2-methyllactato) borate monohydrate*, Acta Crystallographica Section E, Structure Reports Online, vol. 68, No. 6, Jun. 15, 2012, pp. m749-sup-7, XP 55147472A.

Xu, Wu, et al, *Ionic Liquids of Chelated Orthoborates as Model Ionic Glassformers*, The Journal of Physical Chemistry B, vol. 107, No. 42, Sep. 27, 2003, pp. 11749-11756, XP55147463A.

Dissertation et al, *Die Synthese und elektrochemische Charakterisierung von neuen stabilen Lithiumsalzen mit organischen Anionen und Untersuchungen an Polymer-Gelelektrolyten*, (2003), Lithium-bislactoborat: p. 91, XP 055147562, (180 pages).

Patent Abstracts of Japan, and English machine translation of Japanese Publication 2009-266644 dated Nov. 12, 2009, (13 pages).

ADDITIVE FOR ELECTROLYTE AND ELECTROLYTE AND LITHIUM SECONDARY BATTERY

CROSS-REFERENCE TO RELATED APPLICATION

This application claims priority to and the benefit of U.S. Provisional Application No. 61/842,250, filed on Jul. 2, 2013 in the U.S. Patent and Trademark Office, the entire content of which is incorporated herein by reference.

BACKGROUND

1. Field

An additive for an electrolyte, an electrolyte including the additive, and a lithium secondary battery including the electrolyte are disclosed.

2. Description of the Related Art

Batteries transform chemical energy generated from an electrochemical redox reaction of a chemical material in the battery into electrical energy. Such batteries are classified as a primary battery, which should be disposed after the energy of the battery is all consumed, or a rechargeable battery, which can be recharged and discharged many times.

The rechargeable battery can be charged/discharged many times based on the reversible transformation between chemical energy and electrical energy.

Recent developments in high-tech electronics have allowed electronic devices to become small and light in weight, which leads to an increase in the portability of such electronic devices.

As a power source for such portable electronic devices, the demand for batteries with high energy density are increasing and research related to lithium rechargeable batteries is briskly under progress.

A lithium secondary battery is fabricated by injecting an electrolyte into a battery cell, which includes a positive electrode including a positive active material capable of intercalating/deintercalating lithium and a negative electrode including a negative active material capable of intercalating/deintercalating lithium.

An electrolyte may include an organic solvent in which a lithium salt is dissolved, and may include additional compounds in order to improve electrolyte performance.

SUMMARY

An aspect of an embodiment according to the present invention provides an additive for an electrolyte capable of improving battery performance.

Another aspect of an embodiment according to the present invention provides an electrolyte for a lithium secondary battery including the additive for an electrolyte.

Yet another aspect of an embodiment according to the present invention provides a lithium secondary battery including the electrolyte.

According to one embodiment of the present invention, an additive, the additive being for an electrolyte, is represented by the following Chemical Formula 1.

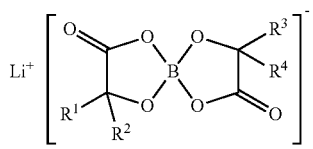

Chemical Formula 1

In the above Chemical Formula 1, $R^1$ to $R^4$ are each independently hydrogen or a non-polar hydrocarbon group.

The non-polar hydrocarbon group may be a C1 to C10 alkyl group, a C3 to C12 cycloalkyl group, a C6 to C20 aryl group, or a combination thereof.

The non-polar hydrocarbon group may be a C1 to C4 alkyl group.

The $R^1$ to $R^4$ of the Chemical Formula 1 may be each independently hydrogen, a methyl group, an ethyl group, a propyl group, a butyl group, an isopropyl group, or an isobutyl group.

Each of $R^1$ and $R^4$ may be hydrogen, and $R^2$ and $R^3$ may be hydrogen, a methyl group, an ethyl group, a propyl group, a butyl group, an isopropyl group, or an isobutyl group.

In Chemical Formula 1, $R^1$ and $R^4$ may be the same, and $R^2$ and $R^3$ may be the same, or $R^1$ and $R^3$ may be the same, and $R^2$ and $R^4$ may be the same.

The additive may be represented by one of the following Chemical Formulae 1a to 1c:

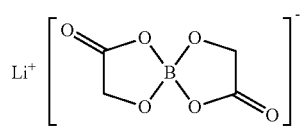

Chemical Formula 1a

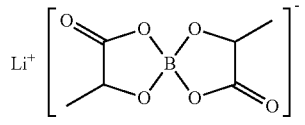

Chemical Formula 1b

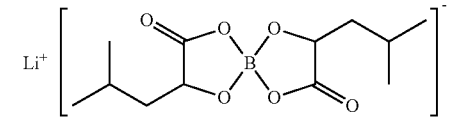

Chemical Formula 1c

According to another embodiment, an electrolyte, the electrolyte being for a lithium secondary battery, includes the additive represented by the Chemical Formula 1, a non-aqueous organic solvent, and a lithium salt.

The additive may be included in the electrolyte in an amount in a range of about 0.001 to 10 wt %, based on the total amount of the electrolyte.

According to another embodiment, a lithium secondary battery includes a positive electrode, a negative electrode facing the positive electrode, and a separator between the positive electrode and the negative electrode, the separator being impregnated with the electrolyte including the additive.

BRIEF DESCRIPTION OF THE DRAWINGS

The accompanying drawings, together with the specification, illustrate embodiments of the present invention, and, together with the description, serve to explain the principles of the present invention.

DETAILED DESCRIPTION

Figure 1:
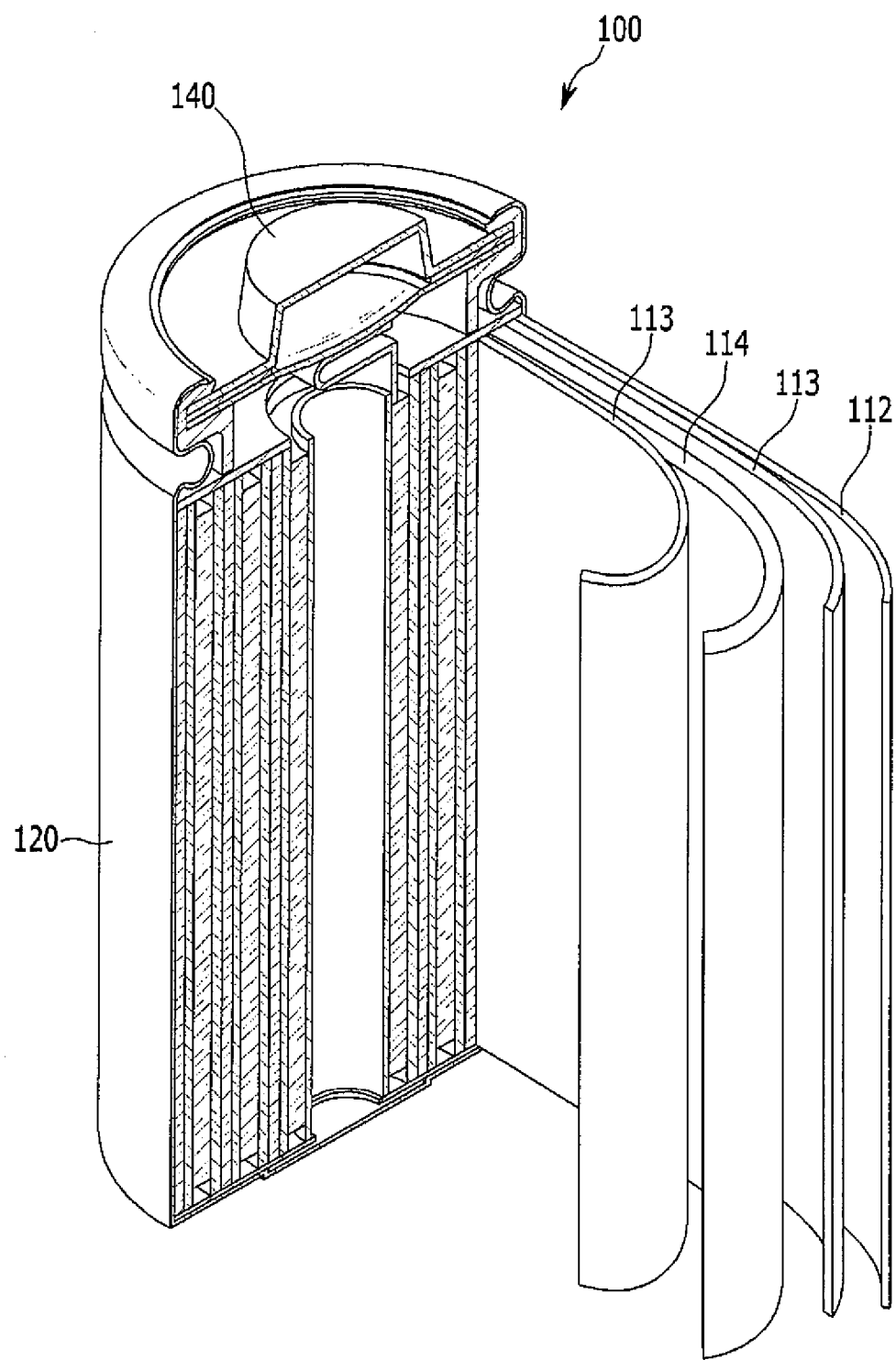
FIG. 1 is a schematic view showing a lithium secondary battery according to one embodiment.

Hereinafter, embodiments of the present invention will be described in detail so that a person skilled in the art would understand the general principles applicable to the present disclosure.

The subject matter of this disclosure may, however, be embodied in many different forms and should not construed as being limited to the embodiments set forth herein.

In this specification, as used herein, when a definition is not otherwise provided, the term "substituted" may refer to one substituted with a substituent selected from a halogen atom (F, Br, Cl or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

In this specification, as used herein, when a definition is not otherwise provided, the term "hetero" may refer to one including 1 to 3 heteroatoms selected from, N, O, S, and P.

As used herein, when a definition is not otherwise provided, the term "non-polar group" may refer to a functional group in which each atom of the functional group is bonded to another atom having a similar electronegativity (e.g., carbon being bonded to hydrogen). Also, in the context of the present application, when a first element is referred to as being "on" a second element, it can be directly on the second element or be indirectly on the second element with one or more intervening elements interposed therebetween. Expressions such as "at least one of," when preceding a list of elements, modify the entire list of elements and do not modify the individual elements on the list. Further, the use of "may" when describing embodiments of the present invention refers to "one or more embodiments of the present invention."

Hereinafter, embodiments of an additive for an electrolyte are described.

An additive for an electrolyte according to one embodiment may be a compound represented by the following Chemical Formula 1:

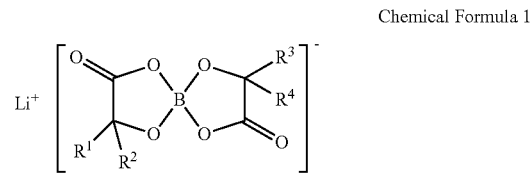

Chemical Formula 1

In Chemical Formula 1, $R^1$ to $R^4$ are each independently hydrogen or a non-polar hydrocarbon group.

The non-polar hydrocarbon group may be, for example, a C1 to C10 alkyl group, a C3 to C12 cycloalkyl group, a C6 to C20 aryl group or a combination thereof. For example, the non-polar hydrocarbon group may be a C1 to C4 alkyl group.

In some embodiments, $R^1$ to $R^4$ are each independently, for example, hydrogen, a methyl group, an ethyl group, a propyl group, a butyl group, an isopropyl group, or an isobutyl group.

For example, $R^1$ and $R^3$ may be each independently hydrogen, and $R^2$ and $R^4$ may be each independently hydrogen, a methyl group, an ethyl group, a propyl group, a butyl group, an isopropyl group, or an isobutyl group. In some embodiments, each of $R^1$ and $R^4$ is hydrogen, and $R^2$ and $R^3$ are independently hydrogen, a methyl group, an ethyl group, a propyl group, a butyl group, an isopropyl group, or an isobutyl group. In some embodiments, $R^1$ and $R^4$ are the same and $R^2$ and $R^3$ are the same, or $R^1$ and $R^3$ are the same and $R^2$ and $R^4$ are the same.

Examples of the compound represented by the above Chemical Formula 1 include organoborates having a non-polar group, such as groups having a carbon-hydrogen bond, in its structure and may have improved electrochemical characteristics when added to an electrolyte.

When an electrolyte including a lithium salt is reduced during the charge and discharge of a battery and forms a passivation film, referred to as a solid electrolyte interface (SEI) film, on the surface of the positive and/or negative electrode, the compound represented by the Chemical Formula 1 includes a non-polar group and may form a non-polar part on a surface of the passivation film.

Accordingly, the passivation film decreases a reaction of the positive and/or negative electrode with the electrolyte and thus may effectively decrease or prevent the electrolyte from being permeated through the passivation film.

In addition, the passivation film has less reactivity with lithium ions and may prevent movement deterioration of the lithium ions (or reduce the amount of movement deterioration of the lithium ions).

The additive for an electrolyte may be, for example, a compound represented by one of the following Chemical Formulae 1a to 1c, but the additive is not limited thereto.

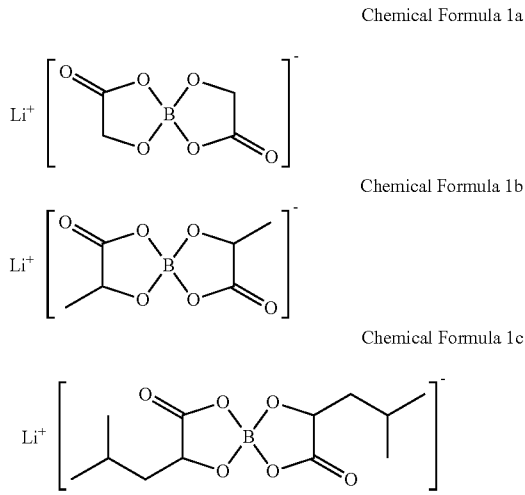

Chemical Formula 1a

Chemical Formula 1b

Chemical Formula 1c

According to another embodiment, an electrolyte for a lithium secondary battery includes the additive for an electrolyte represented by Chemical Formula 1, a non-aqueous organic solvent, and a lithium salt.

The additive represented by the above Chemical Formula 1 may be included in the electrolyte in an amount in a range of about 0.001 to 10 wt %, based on the total amount of the electrolyte.

When the additive is included within the foregoing range, solubility in the electrolyte as well as the aforementioned effect may be secured.

For example, the additive may be included in the electrolyte in an amount in a range of about 0.1 to 5 wt %, based on the total amount of the electrolyte, and be within the above-described range.

In some embodiments, the non-aqueous organic solvent serves as a medium for transmitting ions taking part in the electrochemical reaction of a battery.

The non-aqueous organic solvent may include a carbonate-based, ester-based, ether-based, ketone-based, alcohol-based, and/or aprotic solvent.

The carbonate-based solvent may include dimethyl carbonate (DMC), diethyl carbonate (DEC), dipropyl carbonate (DPC), methylpropyl carbonate (MPC), ethylpropyl carbonate (EPC), methylethyl carbonate (MEC), ethylene carbonate (EC), propylene carbonate (PC), butylene carbonate (BC), and/or the like, and the ester-based solvent may include methyl acetate, ethyl acetate, n-propyl acetate, dimethylacetate, methylpropionate, ethylpropionate, gamma-butyrolactone, decanolide, gamma-valerolactone, mevalonolactone, caprolactone, and/or the like.

The ether-based solvent may include dibutyl ether, tetraglyme, diglyme, dimethoxyethane, 2-methyltetrahydrofuran, tetrahydrofuran, and the like, and the ketone-based solvent may include cyclohexanone, and/or the like.

The alcohol-based solvent may include ethanol, isopropyl alcohol, and/or the like, and the aprotic solvent may include nitriles such as R—CN (wherein R is a C2 to C20 linear, branched, or cyclic hydrocarbon group, and may include a double bond, an aromatic ring, or an ether bond), amides such as dimethylformamide, dimethylacetamide, dioxolanes such as 1,3-dioxolane, sulfolanes, and the like.

The non-aqueous organic solvent may be used singularly or in a mixture. When the organic solvent is used in a mixture, the mixture ratio may be controlled in accordance with a suitable (or desirable) battery performance.

In some embodiments, the carbonate-based solvent is prepared by mixing a cyclic carbonate and a linear carbonate.

In some embodiments, the cyclic carbonate and the linear carbonate are mixed together in the volume ratio in a range of about 1:1 to about 1:9. Within the foregoing range, performance of the electrolyte may be improved.

The non-aqueous organic solvent may further include an aromatic hydrocarbon-based organic solvent as well as the carbonate based solvent.

In some embodiments, the carbonate-based solvent and the aromatic hydrocarbon-based organic solvent are mixed together in a volume ratio in a range of about 1:1 to about 30:1.

Examples of the aromatic hydrocarbon-based organic solvent include benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 2,3-difluorotoluene, 2,4-difluorotoluene, 2,5-difluorotoluene, 2,3,4-trifluorotoluene, 2,3,5-trifluorotoluene, chlorotoluene, 2,3-dichlorotoluene, 2,4-dichlorotoluene, 2,5-dichlorotoluene, 2,3,4-trichlorotoluene, 2,3,5-trichlorotoluene, iodotoluene, 2,3-diiodotoluene, 2,4-diiodotoluene, 2,5-diiodotoluene, 2,3,4-triiodotoluene, 2,3,5-triiodotoluene, xylene, and a combination thereof.

In some embodiments, the lithium salt is dissolved in an organic solvent, supplies lithium ions in a battery, operates a basic operation of the lithium secondary battery, and improves lithium ion transportation between positive and negative electrodes of the battery.

Examples of such a lithium salt include one or more of $LiPF_6$, $LiBF_4$, $LiSbF_6$, $LiAsF_6$, $LiN(SO_2C_2F_5)_2$, $Li(CF_3SO_2)_2N$, $LiN(SO_3C_2F_5)_2$, $LiC_4F_9SO_3$, $LiClO_4$, $LiAlO_2$, $LiAlCl_4$, $LiN(C_xF_{2x+1}SO_2)$, wherein, x and y are natural numbers, LiCl, and LiI.

The lithium salt may be used (e.g., included in the electrolyte) at a concentration in a range of about 0.1 to about 2.0M.

When the lithium salt is included in the electrolyte within the above concentration range, it may improve electrolyte performance and lithium ion mobility due to suitable (or desired) electrolyte conductivity and viscosity.

Hereinafter, a lithium secondary battery according to another embodiment is described referring to FIG. 1.

FIG. 1 is a schematic view of a lithium secondary battery according to one embodiment.

Referring to FIG. 1, a lithium secondary battery 100 according to one embodiment includes: a battery cell including a positive electrode 114, a negative electrode 112 facing the positive electrode 114, a separator 113 interposed between the positive electrode 114 and negative electrode 112, and an electrolyte for a lithium secondary battery impregnating the positive electrode 114, the negative electrode 112, and the separator 113; a battery case 120 including the battery cell; and a sealing member 140 sealing the battery case 120.

The positive electrode 114 includes a current collector and a positive active material layer disposed on the current collector.

The current collector may include an aluminum foil, but the current collector is not limited thereto.

The positive active material layer includes a positive active material, a binder, and a conductive material.

The positive active material includes compounds (lithiated intercalation compounds) that reversibly intercalate and deintercalate lithium ions.

Examples of the compounds include those represented by the following chemical formulae:

$Li_aA_{1-b}X_bD_2$ (0.90≤a≤1.8, 0≤b≤0.5); $Li_aA_{1-b}X_bO_{2-c}D_c$ (0.90≤a≤1.8, 0≤b≤0.5, 0≤c≤0.05); $Li_aE_{1-b}X_bO_{2-c}D_c$ (0.90≤a≤1.8, 0≤b≤0.5, 0≤c≤0.05); $Li_aE_{2-b}X_bO_{4-c}D_c$ (0.90≤a≤1.8, 0≤b≤0.5, 0≤c≤0.05); $Li_aNi_{1-b-c}Co_bX_cD_\alpha$ (0.90≤a≤1.8, 0≤b≤0.5, 0≤c≤0.5, 0≤α≤2); $Li_aNi_{1-b-c}Co_bX_cO_{2-\alpha}T_\alpha$ (0.90≤a≤1.8, 0≤b≤0.5, 0≤c≤0.05, 0≤α≤2); $Li_aNi_{1-b-c}Co_bX_cO_{2-\alpha}T_2$ (0.90≤a≤1.8, 0≤b≤0.5, 0≤0.05, 0≤α≤2); $Li_aNi_{1-b-c}Mn_bX_cD_\alpha$ (0.90≤a≤1.8, 0≤b≤0.5, 0≤c≤0.05, 0≤a≤2); $Li_aNi_{1-b-c}Mn_bX_cO_{2-\alpha}T_\alpha$ (0.90≤a≤1.8, 0≤b≤0.5, 0≤c≤0.05, 0≤α≤2); $Li_aNi_{1-b-c}Mn_bX_cO_{2-\alpha}T_2$ (0.90≤a≤1.8, 0≤b 0.5, 0≤c≤0.05, 0≤a≤2); $Li_aNi_bE_cG_dO_2$ (0.90≤a≤1.8, 0≤b≤0.9, 0≤c≤0.5, 0.001≤d≤0.1); $Li_aNi_bCo_cMn_dG_eO_2$ (0.90≤a≤1.8, 0≤b≤0.9, 0≤c≤0.5, 0≤d≤0.5, 0.001≤e≤0.1); $Li_aNiG_bO_2$ (0.90≤a≤1.8, 0.001≤b≤0.1); $Li_aCoG_bO_2$ (0.90≤a≤1.8, 0.001≤b≤0.1); $Li_aMn_{1-b}G_bO_2$ (0.90≤a≤1.8, 0.001≤b≤0.1); $Li_aMn_2G_bO_4$ (0.90≤a≤1.8, 0.001≤b≤0.1); $Li_aMn_{1-g}G_gPO_4$ (0.90≤a≤1.8, 0≤g≤0.5); $QO_2$; $QS_2$; $LiQS_2$; $V_2O_5$; $LiV_2O_5$; $LiZO_2$; $LiNiVO_4$; $Li_{(3-f)}J_2(PO_4)_3$ (0≤f≤2); $Li_{(3-f)}Fe_2(PO_4)_3$ (0≤f≤2); and $Li_aFePO_4$ (0.90≤a≤1.8)

In the above chemical formulae, A is selected from Ni, Co, Mn, and a combination thereof; X is selected from Al, Ni, Co, Mn, Cr, Fe, Mg, Sr, V, a rare earth element, and a combination thereof; D is selected from O, F, S, P, and a combination thereof; E is selected from Co, Mn, and a combination thereof; T is selected from F, S, P, and a combination thereof; G is selected from Al, Cr, Mn, Fe, Mg, La, Ce, Sr, V, and a combination thereof; Q is selected from Ti, Mo, Mn, and a combination thereof; Z is selected from Cr, V, Fe, Sc, Y, and a combination thereof; and J is selected from V, Cr, Mn, Co, Ni, Cu, and a combination thereof.

The positive active material may be a compound with a coating layer on a surface of the compound or a mixture of an active material and a compound with a coating layer thereon.

The coating layer may include at least one coating element compound selected from the group consisting of an oxide and a hydroxide of the coating element, an oxyhydroxide of the coating element, an oxycarbonate of the coating element, and a hydroxycarbonate of the coating element.

The coating element compound of the coating layer may be either amorphous or crystalline.

The coating element included in the coating layer may be Mg, Al, Co, K, Na, Ca, Si, Ti, V, Sn, Ge, Ga, B, As, Zr, or a mixture thereof.

The coating process may include any suitable, conventional processes (e.g., spray coating, immersing), unless it causes any unsuitable side effects on the properties of the positive active material, which is well known to those who have ordinary skill in this art and will not be illustrated in more detail.

The positive active material may be included in an amount in a range of about 90 wt % to 98 wt %, based on the total amount of the positive active material layer.

The binder improves binding properties of the positive active material particles to one another and to a current collector. Examples of the binder include polyvinyl alcohol, carboxylmethylcellulose, hydroxypropylcellulose, diacetylcellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like, but the binder is not limited thereto.

The conductive material improves electrical conductivity of a negative electrode. Any suitable electrically conductive material may be used as a conductive agent unless it causes an unsuitable chemical change in the battery. Examples of the conductive material include a carbon-based material such as natural graphite, artificial graphite, carbon black, acetylene black, ketjen black, a carbon fiber, or the like; a metal-based material of a metal powder or a metal fiber, and the like such as copper, nickel, aluminum, silver, or the like; a conductive polymer material such as a polyphenylene derivative or the like; and a mixture thereof.

The binder and conductive material may each be included in an amount in a range of about 1 wt % to 5 wt %, based on the total amount of the positive active material layer.

The positive electrode 114 may be manufactured according to a method of preparing a positive active material slurry by mixing the positive active material, the binder, and the conductive material in a solvent, and coating the positive active material slurry on a current collector.

Examples of the solvent include N-methylpyrrolidone and the like, but the solvent is not limited thereto.

The positive electrode manufacturing method is well known and thus, is not described in more detail in the present specification.

The negative electrode 112 may include a current collector and a negative active material layer disposed on at least one side of the current collector.

The current collector may include a copper foil, a nickel foil, a stainless steel foil, a titanium foil, a nickel foam, a copper foam, a polymer substrate coated with a conductive metal, or a combination thereof.

The negative active material may include a material that reversibly intercalates/deintercalates lithium ions, a lithium metal, a lithium metal alloy, a material being capable of doping and dedoping lithium, or a transition metal oxide.

The material that reversibly intercalates/deintercalates lithium ions may include a carbon material, and the carbon material may be any, suitable generally-used carbon-based negative active material in a lithium ion rechargeable battery, and examples of the carbon material include crystalline carbon, amorphous carbon, and a mixture thereof.

The crystalline carbon may be non-shaped or sheet, flake, spherical, or fiber shaped natural graphite or artificial graphite, and the amorphous carbon may be a soft carbon (carbon obtained by sintering at a low temperature), a hard carbon, mesophase pitch carbonization products, fired coke, or the like.

Examples of the lithium metal alloy include lithium and a metal selected from Na, K, Rb, Cs, Fr, Be, Mg, Ca, Sr, Si, Sb, Pb, In, Zn, Ba, Ra, Ge, Al, and Sn.

The material being capable of doping and dedoping lithium may include Si, $SiO_x$, (0<x<2), a Si—C composite, a Si-Q alloy (wherein Q is an alkali metal, an alkaline-earth metal, Group 13 to Group 16 elements, a transition element, a rare earth element, or a combination thereof, and is not Si), Sn, $SnO_2$, a Sn—C composite, Sn—R (wherein R is an alkali metal, an alkaline-earth metal, Group 13 to Group 16 elements, a transition element, a rare earth element, or a combination thereof, and not Sn), and/or the like, and at least one thereof may be used as a mixture with $SiO_2$.

The elements Q and R may include Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, or a combination thereof.

The transition metal oxide may include vanadium oxide, lithium vanadium oxide, and/or the like.

The binder improves properties of binding active material particles with one another and a negative active material with a current collector.

The binder may be a non-water-soluble binder, a water-soluble binder, or a combination thereof.

The non-water-soluble binder may be polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, polyamideimide, polyimide, or a combination thereof.

The water-soluble binder may be a styrene-butadiene rubber, an acrylated styrene-butadiene rubber, polyvinyl alcohol, sodium polyacrylate, a copolymer of propylene and C2 to C8 olefin, a copolymer of (meth)acrylic acid and (meth)acrylic acid alkyl ester, or a combination thereof.

When the water-soluble binder is used as a negative electrode binder, a cellulose-based compound may be further used to provide viscosity.

Examples of the cellulose-based compound include one or more of carboxylmethyl cellulose, hydroxypropylmethyl cellulose, methyl cellulose, or alkali metal salts thereof.

The alkali metal may be Na, K, or Li.

A thickener may be included in the negative active material layer in an amount in a range of about 0.1 to about 3 parts by weight based on 100 parts by weight of the binder.

In some embodiments, the conductive material is included in the negative active material layer to provide electrode conductivity, and any suitable electrically conductive material may be used as a conductive material unless it causes a chemical change in the battery. Examples of the conductive material include a carbon-based material such as natural graphite, artificial graphite, carbon black, acetylene black, ketjen black, a carbon fiber or the like; a metal-based material of metal powder or metal fiber including copper, nickel, aluminum, silver, and the like; a conductive polymer such as a polyphenylene derivative; and a mixture thereof.

The negative electrode may be manufactured by a general process including preparing a negative active material slurry by mixing a negative active material, a binder, and optionally a conductive agent in a solvent, coating the negative active material slurry on a current collector, followed by drying and compressing.

Examples of the solvent may be N-methylpyrrolidone or water, but the solvent is not limited thereto.

The negative electrode manufacturing method is well known and thus, is not described in more detail in the present specification.

The separator 113 separates the positive electrode 114 and negative electrode 112 and provides a path for transferring lithium ions and may be any suitable separator that is generally used in a lithium ion battery.

In other words, the separator may have low resistance against electrolyte ions and excellent electrolyte moisturizing capability.

For example, the separator may be selected from a glass fiber, polyester, TEFLON® (tetrafluoroethylene) (TEFLON® is a registered trademark of E. I. du Pont de Nemours and Company, Wilmington Del.), polyethylene, polypropylene, polytetrafluoroethylene (PTFE), or a combination thereof and may have a non-woven fabric kind or a fabric kind.

For example, a polyolefin-based polymer separator such as polyethylene, polypropylene, or the like is used for a lithium ion battery, a separator coated with a ceramic component or a polymer material may be used to secure heat resistance or mechanical strength, and the separator may be a singular layer or multiple layers.

Rechargeable lithium batteries may be classified as lithium ion batteries, lithium ion polymer batteries, or lithium polymer batteries according to the presence of a separator and the kind of electrolyte used in the battery, and the rechargeable lithium batteries may also be classified as cylindrical, prismatic, coin-shape, or pouch-shape batteries according to the shape of the battery, and may be classified as thin film batteries or bulk batteries.

Structures and manufacturing methods for lithium ion batteries pertaining to this disclosure are well known in the art.

The electrolyte is the same (or substantially the same) as described above.

Hereinafter, the above-described aspects of the present disclosure are illustrated in more detail with reference to examples.

Preparation of Additive

Synthesis Example 1

6.0 g (78 mmol) of glycolic acid, 1.7 g (39 mmol) of lithium hydroxide, and 2.4 g (39 mmol) of boronic acid were mixed in an aqueous solution, and the mixture was agitated at a temperature in a range of 180° C. to 200° C. for 12 hours.

Subsequently, after removing the resultant product from the aqueous solution, the resultant product was dried at 80° C. for 48 hours and washed with diethylether, thereby obtaining a compound represented by the following Chemical Formula 1a.

Chemical Formula 1a

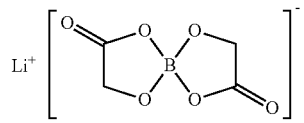

$^1$H NMR (DMSO-d6, 400 MHz): δ 3.92 (2H)

Synthesis Example 2

Lactic acid (85% in water), lithium hydroxide, and boronic acid in a mole ratio of 2:1:1 were mixed in an aqueous solution, and the mixture was agitated at a temperature in a range of 180° C. to 200° C. for 12 hours.

Subsequently, after removing the resultant product from the aqueous solution, the resultant product was dried at 80° C. for 48 hours and washed with diethylether, thereby obtaining a compound represented by the following Chemical Formula 1 b.

Chemical Formula 1b

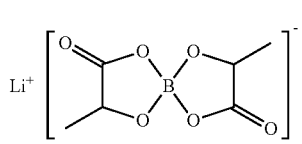

$^1$H NMR (DMSO-d6, 400 MHz): δ 3.89 (1H), 1.12 (3H)

Synthesis Example 3

8.0 g (60 mmol) of leucic acid, 1.3 g (30 mmol) of lithium hydroxide, and 1.9 g (30 mmol) of boronic acid were mixed in an aqueous solution, and the mixture was agitated at a temperature in a range of 180° C. to 200° C. for 12 hours.

Subsequently, after removing the resultant product from the aqueous solution, the resultant product was dried at 80° C. for 48 hours and washed with diethylether, thereby obtaining a compound represented by the following Chemical Formula 1c.

Chemical Formula 1c

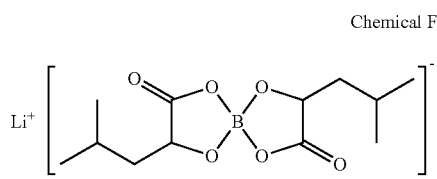

$^1$H NMR (DMSO-d6, 400 MHz): δ 3.82 (1H), 1.81 (1H), 1.61 (2H), 0.92 (6H)

Preparation of Electrolyte

Example 1

An electrolyte for a lithium secondary battery was prepared by adding 1.3M LiPF$_6$ lithium salt to a mixed solvent prepared by mixing ethylene carbonate (EC), ethylmethyl carbonate (EMC), and dimethyl carbonate (DMC) in a ratio of 3/5/2 (v/v/v) and then, adding 1 wt % of the compound according to Synthesis Example 1 to the mixture.

Example 2

An electrolyte for a lithium secondary battery was prepared according to the same method as Example 1 except for using the compound according to Synthesis Example 2 instead of the compound according to Synthesis Example 1.

Example 3

An electrolyte for a lithium secondary battery was prepared according to the same method as Example 1 except for using the compound according to Synthesis Example 3 instead of the compound according to Synthesis Example 1.

Comparative Example 1

An electrolyte for a lithium secondary battery was prepared according to the same method as Example 1 except that the compound according to Synthesis Example 1 was not added.

Evaluation—1: Cycle-Life

The electrolytes according to Examples 1 to 3 and Comparative Example 1 were respectively used to manufacture lithium secondary battery cells.

Herein, a positive electrode was manufactured by mixing 97.4 wt % of LiCoO$_2$, 1.3 wt % of polyvinylidene fluoride (PVdF), and 1.3 wt % of acetylene black in N-methylpyrrolidone (NMP) to prepare a positive active material slurry and coating the positive active material slurry on an aluminum current collector.

A negative electrode was manufactured by mixing 98.0 wt % of artificial graphite, 1.0 wt % of a styrenebutadiene rubber (SBR), and 1.0 wt % of carboxylmethylcellulose (CMC) in water to prepare a negative active material slurry and coating the negative active material slurry on a copper current collector.

The lithium secondary battery cells including the electrolytes according to Examples 1 to 3 and Comparative Example 1 were charged and discharged 100 times under a current of 1 C at 25° C., and a discharge capacity of each of the lithium secondary battery cells was measured at each cycle.

Figure 2:
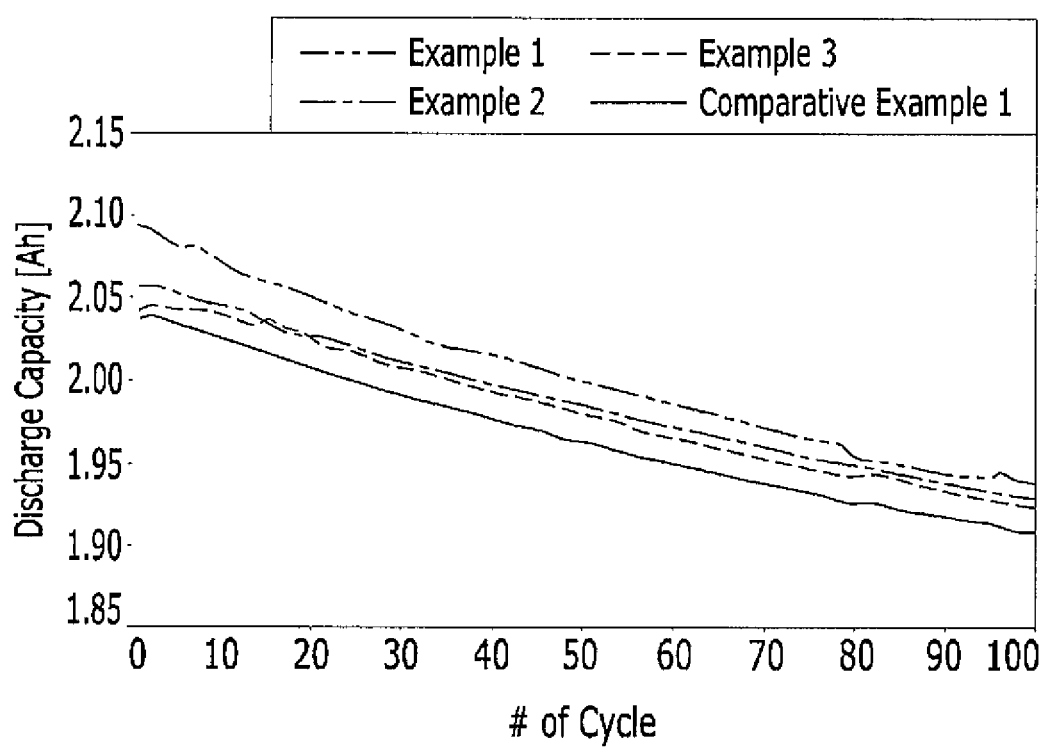
FIG. 2 is a graph showing discharge capacity of lithium secondary batteries respectively including electrolytes prepared according to Examples 1 to 3 and Comparative Example 1 depending on a cycle.

FIG. 2 is a graph showing discharge capacity of the lithium secondary battery cells including the electrolytes prepared according to Examples 1 to 3 and Comparative Example 1 depending on a cycle.

Referring to FIG. 2, the lithium secondary battery cells including the electrolytes prepared according to Examples 1 to 3 had higher discharge capacity retention after 100 cycles than the lithium secondary battery cell including the electrolyte prepared according to Comparative Example 1.

Evaluation—2: Self-Discharge

Coin-shape half-cells 1 and 2 respectively including the electrolytes according to Examples 2 and 3 and Comparative Example 1 were manufactured to evaluate self-discharge at a high temperature.

Each coin-shape half-cell 1 respectively included an electrolyte prepared according to Examples 2 and 3 and Comparative Example 1, the above-described LiCoO$_2$ positive electrode, and a lithium metal as a counter electrode.

Each coin-shape half-cell 2 respectively included an electrolyte prepared according to Examples 2 and 3 and Comparative Example 1, the above-described artificial graphite as a negative electrode, and a lithium metal as a counter electrode.

The coin-shape half-cells 1 and 2 were charged up to 4.2V, allowed to stand at 60° C. for 22 days, and their self-discharge degrees were evaluated.

Herein, the self-discharge indicates potential charge decrease of a battery when no current flows in an external circuit and may be used to evaluate high temperature stability of lithium secondary battery cells.

The results are provided in FIGS. 3 to 8.

Figure 3:
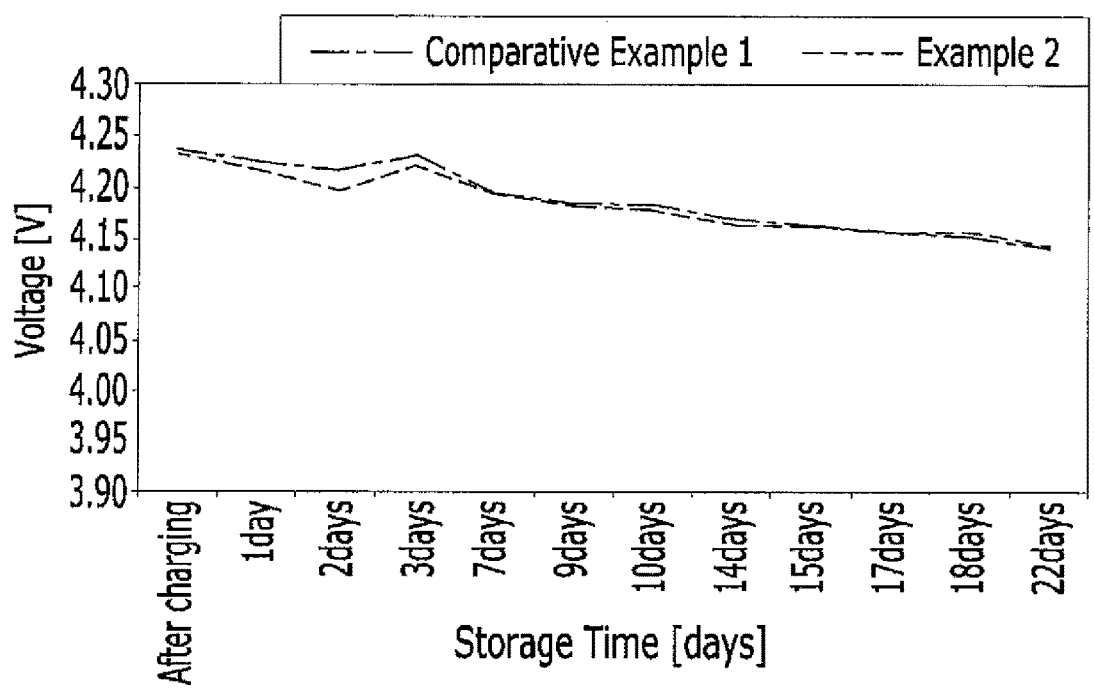
FIG. 3 is a graph showing potential change of coin-shape half-cells 1 respectively including electrolytes prepared according to Example 2 and Comparative Example 1 when being allowed to stand at 60° C. for 22 days.
Figure 4:
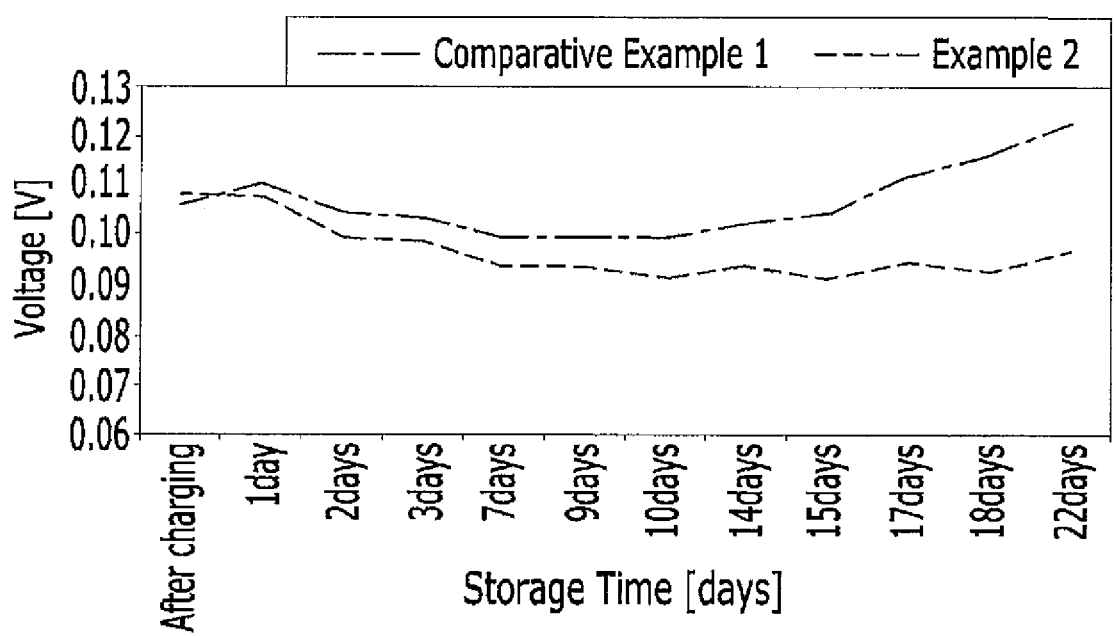
FIG. 4 is a graph showing potential change of coin-shape half-cells 2 respectively including electrolytes prepared according to Example 2 and Comparative Example 1 when being allowed to stand at 60° C. for 22 days.
Figure 5:
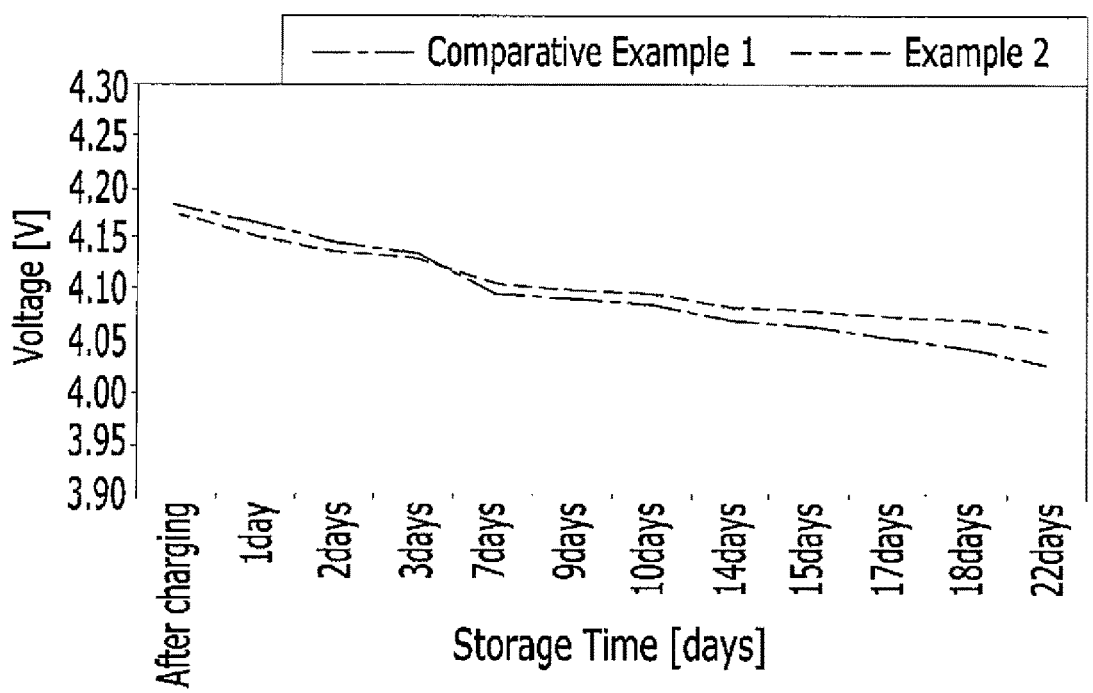
FIG. 5 is a graph showing potential change of lithium secondary battery cells respectively including electrolytes prepared according to Example 2 and Comparative Example 1.
Figure 6:
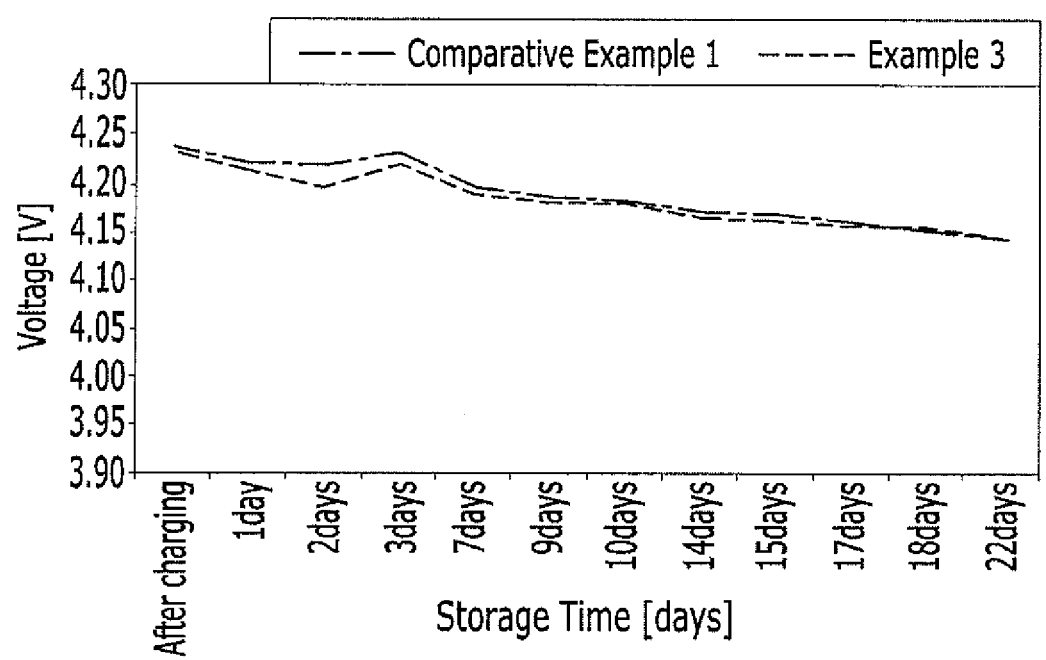
FIG. 6 is a graph showing potential change of coin-shape half-cells 1 respectively including electrolytes prepared according to Example 3 and Comparative Example 1 when being allowed to stand at 60° C. for 22 days.
Figure 7:
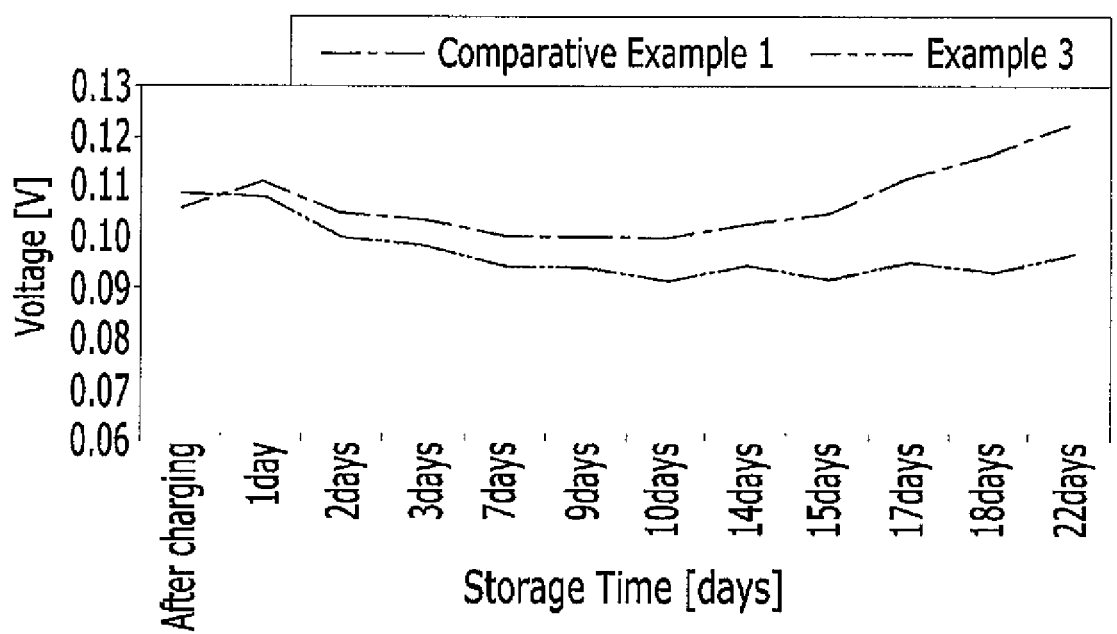
FIG. 7 is a graph showing potential change of coin-shape half-cells 2 respectively including electrolytes prepared according to Example 3 and Comparative Example 1 when being allowed to stand at 60° C. for 22 days.
Figure 8:
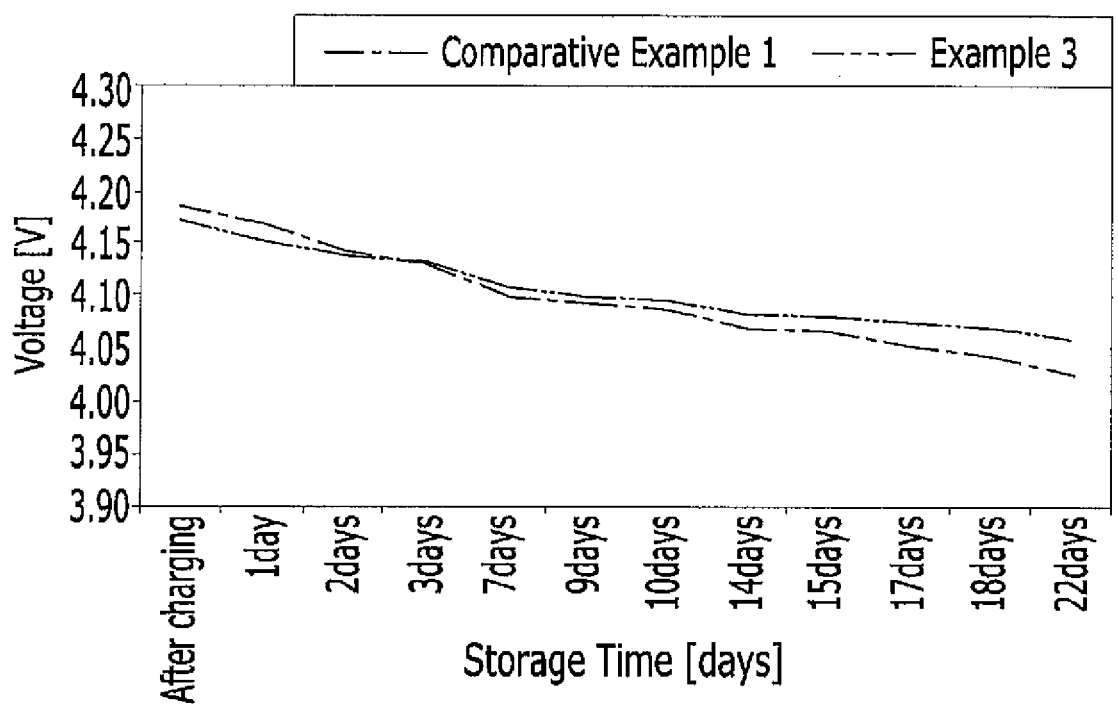
FIG. 8 is a graph showing potential changes of lithium secondary battery cells respectively including electrolytes prepared according to Example 3 and Comparative Example 1.

FIG. 3 is a graph showing potential changes of the coin-shape half-cells 1 respectively including the electrolytes prepared according to Example 2 and Comparative Example 1 when being allowed to stand at 60° C. for 22 days, FIG. 4 is a graph showing potential changes of the coin-shape half-cells 2 respectively including the electrolytes prepared according to Example 2 and Comparative Example 1 when being allowed to stand at 60° C. for 22 days, FIG. 5 a graph showing potential changes of the lithium secondary battery cells respectively including the electrolytes prepared according to Example 2 and Comparative Example 1 when being allowed to stand at 60° C. for 22 days, FIG. 6 is a graph showing potential change of the coin-shape half-cells 1 respectively including the electrolytes prepared according to Example 3 and Comparative Example 1 when being allowed to stand at 60° C. for 22 days, FIG. 7 is a graph showing potential change of the coin-shape half-cells 2 respectively including the electrolytes prepared according to Example 3 and Comparative Example 1 when being allowed to stand at 60° C. for 22 days, and FIG. 8 is a graph showing potential change of the lithium secondary battery cells respectively including the electrolytes prepared according to Example 3 and Comparative Example 1.

In general, when a lithium secondary battery cell is self-discharged, a potential of a lithium secondary battery is decreased as lithium ions are discharged from a negative electrode, while a potential of the charged positive electrode increases.

Referring to FIGS. 3 to 5, the coin-shape half-cells 1 respectively including the electrolytes prepared according to Example 2 and Comparative Example 1 showed similar potential changes, but the coin-shape half-cell 2 including the electrolyte prepared according to Example 2 showed a smaller overall potential change as compared with the coin-shape half-cell 2 including the electrolyte according to Comparative Example 1.

Accordingly, it is believed that the coin-shape half-cell 1 including the electrolyte according to Example 2 turned out to decrease (e.g., reduce) self-discharge at a high temperature by forming a stable solid electrolyte film on a surface of the negative electrode.

Since the potential difference of the lithium secondary battery cells respectively including the electrolytes prepared according to Example 2 and Comparative Example 1 were evaluated by a potential difference between coin-shape half-cells 1 and 2, the lithium secondary battery cell including the electrolyte prepared according to Example 2 showed smaller self-discharge than that of the lithium secondary battery cell including the electrolyte prepared according to Comparative Example 1 and thus, had high stability at a high temperature.

Likewise, referring to FIGS. 6 to 8, the coin-shape half-cells 1 respectively including the electrolytes prepared according to Example 3 and Comparative Example 1 showed similar potential changes, but the coin-shape half-cell 2 including the electrolyte prepared according to Example 3 showed a smaller overall potential change depending on a storage day (e.g., time) than that of the coin-shape half-cell 2 including the electrolyte prepared according to Comparative Example 1.

Accordingly, it is believed that the coin-shape half-cell 2 including the electrolyte according to Example 3 turned out to decrease (e.g., reduce) self-discharge at a high temperature by forming a stable solid electrolyte film on a surface of the negative electrode.

Since the potential difference of the lithium secondary battery cells respectively including the electrolytes prepared according to Example 3 and Comparative Example 1 were evaluated by a potential difference between coin-shape half-cells 1 and 2, the lithium secondary battery cell including the electrolyte prepared according to Example 3 had a smaller self-discharge than that of the lithium secondary battery including the electrolyte prepared according to Comparative Example 1 and thus, high temperature stability.

Figure 9:
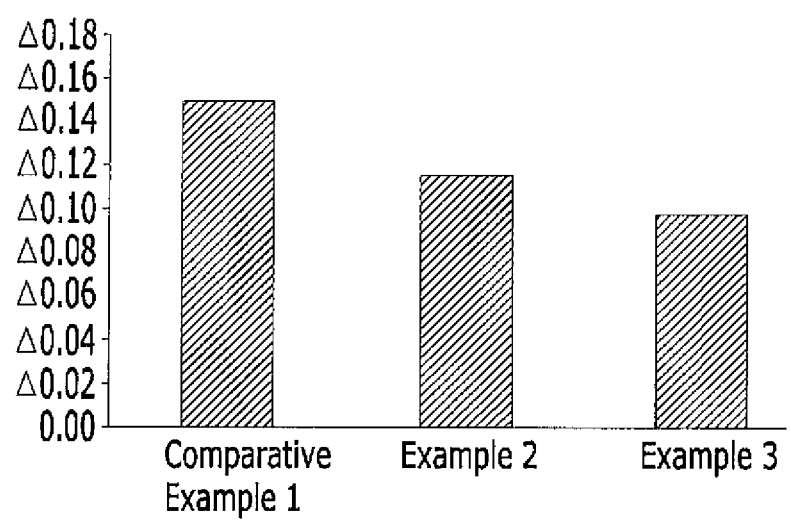
FIG. 9 is a graph showing potential decreases of lithium secondary battery cells respectively including electrolytes prepared according to Examples 2 and 3 and Comparative Example 1 when being allowed to stand at 60° C. for 22 days.

FIG. 9 is a graph showing potential decrease degree of the lithium secondary battery cells respectively including the electrolytes prepared according to Examples 2 and 3 and Comparative Example 1 when being allowed to stand at 60° C. for 22 days.

Referring to FIG. 9, the lithium secondary battery cells respectively including the electrolytes prepared according to Examples 2 and 3 showed a smaller potential decrease degree and, accordingly, a smaller self-discharge, than the lithium secondary battery cell including the electrolyte prepared according to Comparative Example 1.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. An additive, the additive being for an electrolyte for a lithium secondary battery and represented by Chemical Formula 1:

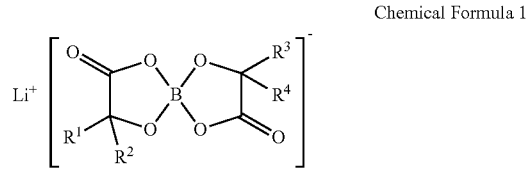

Chemical Formula 1

$R^1$ to $R^4$ each independently being hydrogen or a non-polar hydrocarbon group selected from the group consisting of an ethyl group, a propyl group, a butyl group, an isopropyl group, an isobutyl group, a C3 to C12 cycloalkyl group, a C6 to C20 aryl group, or a combination thereof.

2. The additive of claim 1, wherein the non-polar hydrocarbon group is a C3 to C12 cycloalkyl group, a C6 to C20 aryl group, or a combination thereof.

3. The additive of claim 1, wherein $R^1$ to $R^4$ is each independently hydrogen, an ethyl group, a propyl group, a butyl group, an isopropyl group, or an isobutyl group.

4. The additive of claim 1, wherein each of $R^1$ and $R^4$ is hydrogen, and $R^2$ and $R^3$ are independently hydrogen, an ethyl group, a propyl group, a butyl group, an isopropyl group, or an isobutyl group.

5. The additive of claim 1, wherein $R^1$ and $R^4$ are the same, and $R^2$ and $R^3$ are the same, or wherein $R^1$ and $R^3$ are the same, and $R^2$ and $R^4$ are the same.

6. The additive of claim 1, wherein the additive is represented by Chemical Formulae 1a or 1c:

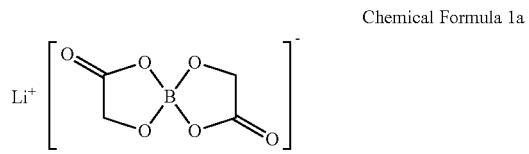

Chemical Formula 1a

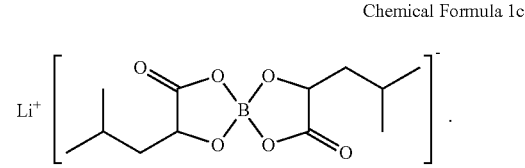

Chemical Formula 1c

7. An electrolyte, the electrolyte being for a lithium secondary battery and comprising:
a non-aqueous organic solvent;
a lithium salt; and
an additive represented by Chemical Formula 1:

Chemical Formula 1

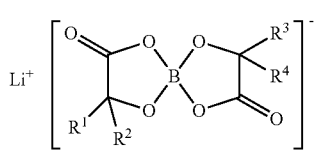

$R^1$ to $R^4$ each independently being hydrogen or a non-polar hydrocarbon group selected from the group consisting of an ethyl group, a propyl group, a butyl group, an isopropyl group, an isobutyl group, a C3 to C12 cycloalkyl group, a C6 to C20 aryl group, or a combination thereof.

8. The electrolyte of claim 7, wherein the additive is present in the electrolyte in an amount in a range of about 0.001 to about 10 wt %, based on the total amount of the electrolyte.

9. The electrolyte of claim 8, wherein the additive is present in the electrolyte in an amount in a range of about 0.1 to about 5 wt %, based on the total amount of the electrolyte.

10. The electrolyte of claim 7, wherein the non-polar hydrocarbon group is a C3 to C12 cycloalkyl group, a C6 to C20 aryl group, or a combination thereof.

11. The electrolyte of claim 7, wherein $R^1$ to $R^4$ is each independently hydrogen, an ethyl group, a propyl group, a butyl group, an isopropyl group, or an isobutyl group.

12. The electrolyte of claim 7, wherein each of $R^1$ and $R^4$ is hydrogen, and $R^2$ and $R^3$ are independently hydrogen, an ethyl group, a propyl group, a butyl group, an isopropyl group, or an isobutyl group.

13. The electrolyte of claim 7, wherein the additive is represented by Chemical Formulae 1a or 1c:

Chemical Formula 1a

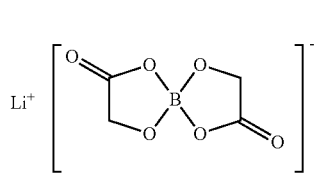

Chemical Formula 1c

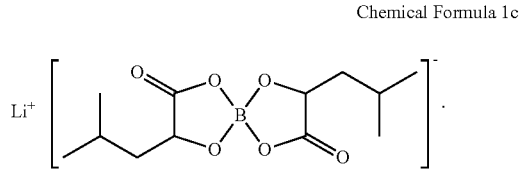

14. A lithium secondary battery comprising:
a positive electrode;
a negative electrode facing the positive electrode; and
a separator between the positive electrode and the negative electrode, the separator being impregnated with an electrolyte comprising an additive represented by Chemical Formula 1:

Chemical Formula 1

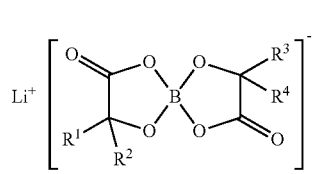

$R^1$ to $R^4$ each independently being hydrogen or a non-polar hydrocarbon group selected from the group consisting of an ethyl group, a propyl group, a butyl group, an isopropyl group, an isobutyl group, a C3 to C12 cycloalkyl group, a C6 to C20 aryl group, or a combination thereof.

15. The lithium secondary battery of claim 14, wherein the additive is present in the electrolyte in an amount in a range of about 0.001 to about 10 wt %, based on the total amount of the electrolyte.

16. The lithium secondary battery of claim 14, wherein the non-polar hydrocarbon group a C3 to C12 cycloalkyl group, a C6 to C20 aryl group, or a combination thereof.

17. The lithium secondary battery of claim 14, wherein $R^1$ to $R^4$ is each independently hydrogen, an ethyl group, a propyl group, a butyl group, an isopropyl group, or an isobutyl group.

18. The lithium secondary battery of claim 14, wherein each of $R^1$ and $R^4$ is hydrogen, and $R^2$ and $R^3$ are independently hydrogen, an ethyl group, a propyl group, a butyl group, an isopropyl group, or an isobutyl group.

19. The lithium secondary battery of claim 14, wherein the additive is represented by Chemical Formulae 1a or 1c:

Chemical Formula 1a

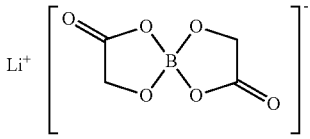

Chemical Formula 1c

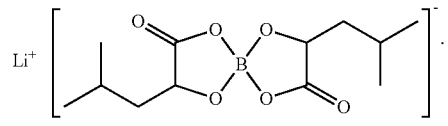

* * * * *